(12) United States Patent
Furenlid et al.

(10) Patent No.: US 10,548,544 B2
(45) Date of Patent: Feb. 4, 2020

(54) ROTATING-SLIT GAMMA-RAY IMAGER AND ASSOCIATED IMAGING METHOD

(71) Applicant: Arizona Board of Regents on Behalf of the University of Arizona, Tucson, AZ (US)

(72) Inventors: Lars R. Furenlid, Tucson, AZ (US); Xin Li, Tucson, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 0 days.

(21) Appl. No.: 15/773,691

(22) PCT Filed: Nov. 4, 2016

(86) PCT No.: PCT/US2016/060675
§ 371 (c)(1),
(2) Date: May 4, 2018

(87) PCT Pub. No.: WO2017/079654
PCT Pub. Date: May 11, 2017

(65) Prior Publication Data
US 2018/0344269 A1    Dec. 6, 2018

Related U.S. Application Data

(60) Provisional application No. 62/250,994, filed on Nov. 4, 2015.

(51) Int. Cl.
*A61B 6/00* (2006.01)
*A61B 6/03* (2006.01)
(Continued)

(52) U.S. Cl.
CPC ............ *A61B 6/4258* (2013.01); *A61B 6/037* (2013.01); *A61B 6/06* (2013.01); *A61B 6/4275* (2013.01);
(Continued)

(58) Field of Classification Search
CPC ......... A61B 6/4258; A61B 6/037; A61B 6/06; A61B 6/4275; A61B 6/4291; A61B 6/5205; G06T 11/006
See application file for complete search history.

(56) References Cited

U.S. PATENT DOCUMENTS

2006/0072801 A1* 4/2006 Bernard Deman ... G06T 11/006
                                                      382/131
2007/0253524 A1   11/2007 Bruder
2008/0061395 A1*  3/2008 Tkaczyk ............... A61B 6/032
                                                      257/443

OTHER PUBLICATIONS

International Search Report of PCT/US2016/060675 dated Jan. 31, 2017, 1 pp.

(Continued)

*Primary Examiner* — Michael C Bryant
(74) *Attorney, Agent, or Firm* — Lathrop Gage LLP

(57) ABSTRACT

A method for forming an optimized image of a subject includes steps of acquiring a plurality of one-dimensional images, generating a measured sinogram from the plurality of one-dimensional images, and determining a plurality of trial images. In the step of acquiring, the method acquires a plurality of one-dimensional images of the subject captured by a rotating-slit imager having (a) a detector, and (b) a slit collimator having a slit oriented at one of a respective plurality of slit-rotation angles, relative to the subject, about a longitudinal axis substantially perpendicular to a front surface of the detector. In the step of determining, the method iteratively determines a plurality of trial images each having a respective trial sinogram. The optimized image is (Continued)

one of the plurality of trial images and its corresponding trial sinogram differs from the measured sinogram by less than a predetermined tolerance.

20 Claims, 14 Drawing Sheets

(51) Int. Cl.
 *A61B 6/06* (2006.01)
 *G06T 11/00* (2006.01)
(52) U.S. Cl.
 CPC .......... *A61B 6/5205* (2013.01); *G06T 11/006* (2013.01); *G06T 11/003* (2013.01); *G06T 2211/424* (2013.01)

(56) References Cited

OTHER PUBLICATIONS

International Preliminary Report on Patentability of PCT/US2016/060675 dated May 8, 2018, 8 pp.

* cited by examiner

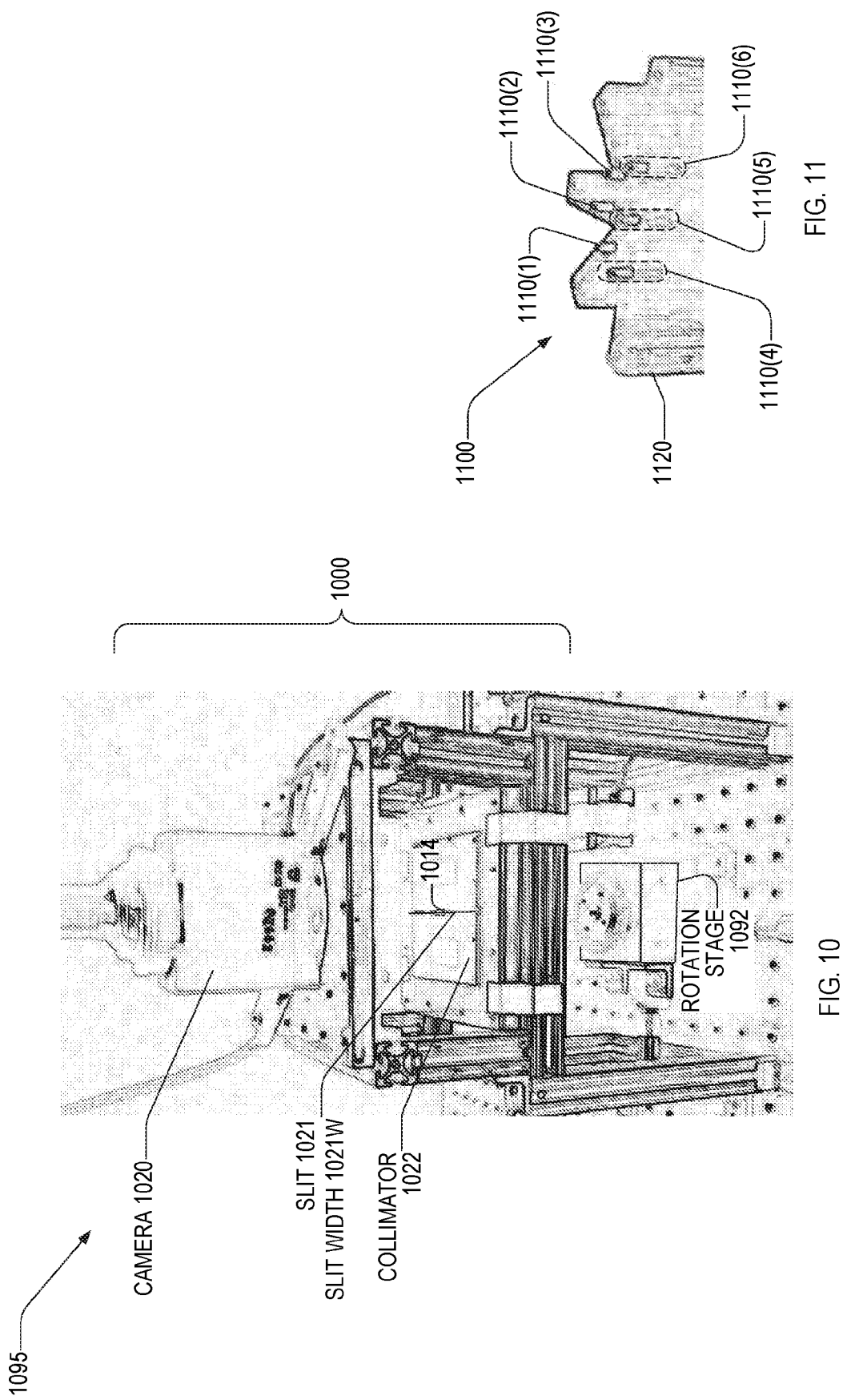

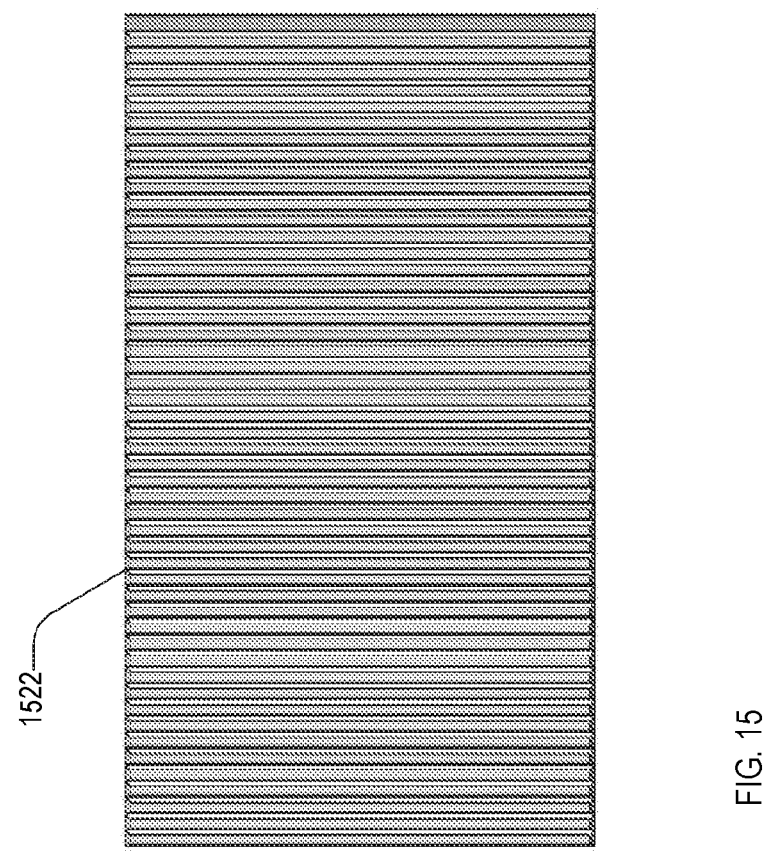
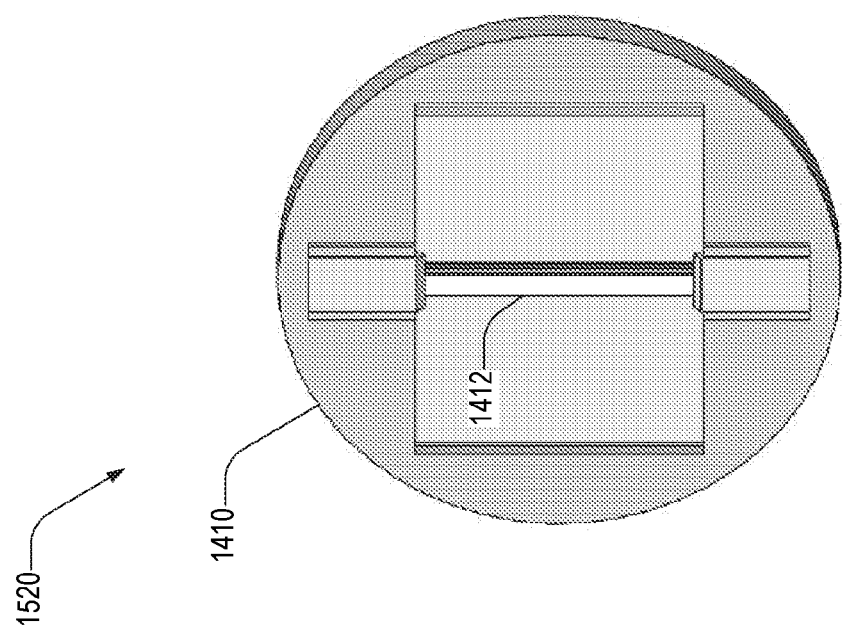
FIG. 15

ROTATING-SLIT GAMMA-RAY IMAGER AND ASSOCIATED IMAGING METHOD

CROSS-REFERENCE TO RELATED APPLICATIONS

This application claims priority to U.S. Provisional Application No. 62/250,994 filed Nov. 4, 2015, which is incorporated by reference in its entirety.

GOVERNMENT INTEREST

This invention was made with government support under Grant No. P41 EB002035, awarded by NIH. The government has certain rights in the invention.

BACKGROUND

Single photon emission computed tomography (SPECT) plays an important role in cancer diagnoses, cardiac-perfusion testing, and drug-delivery studies. Due to the low photon-collection efficiency of current parallel-hole collimators and pinhole apertures, SPECT projection images have high Poisson noise.

SUMMARY

A rotating slit is proposed that addresses at least the aforementioned noise-related limitations.

In a first embodiment, a method for forming an optimized image of a subject includes steps of acquiring a plurality of one-dimensional images, generating a measured sinogram from the plurality of one-dimensional images, and determining a plurality of trial images. In the step of acquiring, the method acquires a plurality of one-dimensional images of the subject captured by a rotating-slit imager having (a) a detector, and (b) a slit collimator having a slit oriented at one of a respective plurality of slit-rotation angles, relative to the subject, about a longitudinal axis substantially perpendicular to a front surface of the detector. In the step of determining, the method iteratively determines a plurality of trial images each having a respective trial sinogram. The optimized image is one of the plurality of trial images and its corresponding trial sinogram differs from the measured sinogram by less than a predetermined tolerance.

In a second embodiment, a rotating-slit gamma-ray imager includes (i) a detector having an array of pixels, (ii) a slit collimator, (iii) a memory storing non-transitory computer-readable instructions, and (iv) a microprocessor. The slit collimator has a slit at least partially aligned with the detector and configured to be oriented at any of a plurality of slit-rotation angles in a plane substantially parallel to the array of pixels. The microprocessor is adapted to execute the instructions to form an optimized image of a subject by implementing the method of the first embodiment.

In a third embodiment, a data processor includes a memory storing non-transitory computer-readable instructions and a microprocessor. The microprocessor is configured to execute the instructions to (i) generate a measured sinogram from a plurality of one-dimensional images, of a subject, captured by a rotating-slit imager having (a) a detector, and (b) a slit collimator having a slit oriented at one of a respective plurality of slit-rotation angles, relative to the subject, about a longitudinal axis substantially perpendicular to a front surface of the detector, and (ii) generate an optimized image by iteratively determining a plurality of trial images each having a respective trial sinogram, the optimized image being one of the trial images, its corresponding trial sinogram differing from the measured sinogram by less than a predetermined tolerance.

BRIEF DESCRIPTION OF THE FIGURES

FIG. 10 shows an experimental setup for a demonstration of the rotating-slit gamma-ray imager of FIG. 1, in an embodiment.

FIG. 11 is a photograph of a phantom that consists of six iodine-125 seeds.

FIG. 15 is a perspective view of a fourth example of the imaging assembly of the rotating-slit gamma-ray imager of FIG. 1.

DETAILED DESCRIPTION OF THE EMBODIMENTS

Rotating-slit pinhole-aperture synthesis yields a much higher photon count image than a physical pinhole, given the same data acquisition time. Slit imaging with a collimator only requires a one-dimensional detector if it is made to rotate with the collimator. The sensitivity advantage becomes very significant as pinhole radius R decreases, because the slit sensitivity scales as 2R, whereas the pinhole sensitivity scales as $R^2$.

Figure 1:
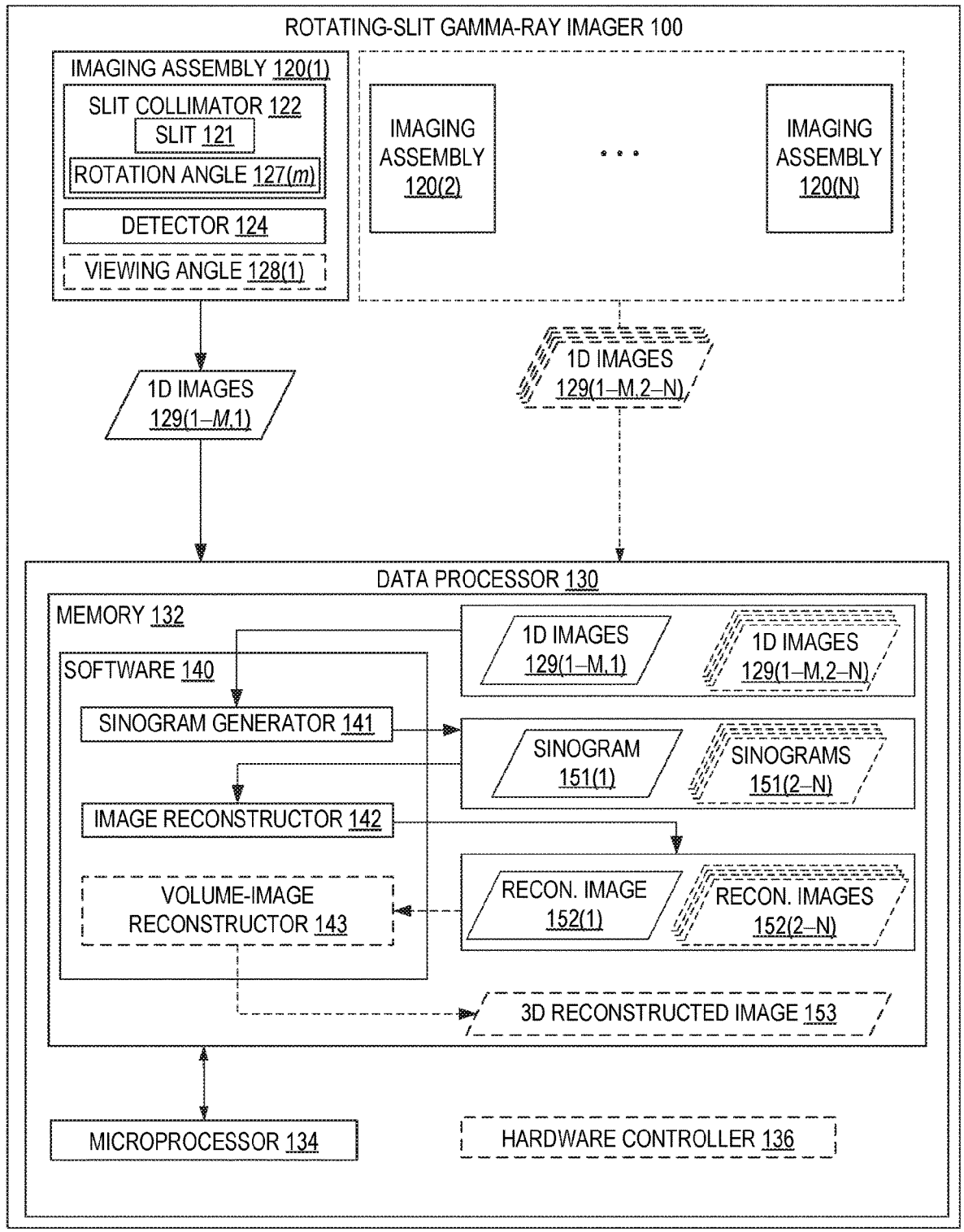
FIG. 1 is a schematic diagram of a rotating-slit gamma-ray imager, in an embodiment.

FIG. 1 is a schematic diagram of an exemplary rotating-slit gamma-ray imager 100. Rotating-slit gamma-ray imager 100 includes one or more imaging assemblies 120. Each imaging assembly 120 includes a slit collimator 122 and a detector 124. Slit collimator 122 includes a slit 121 oriented at a rotation angle 127. Imager 100 also includes a data processor 130 communicatively coupled to each detector 124.

Herein, an element in the figures denoted by a reference numeral suffixed by a parenthetical numeral is an example of the element indicated by the reference numeral. For example, imaging assembly 120(2) is an example (2) of imaging assembly 120. Rotating-slit gamma-ray imager 100 may also include additional imaging assemblies 120(2) to 120(N), where integer N≥2. Each imaging assembly 120 may have a respective viewing angle 128 of a common imaging volume in the field of view of each imaging assembly 120.

Detector 124 is configured to capture a plurality of one-dimensional images 129. In FIG. 1, one-dimensional images 129 from a single imaging assembly 120 include M images indexed by an integer m. Index m∈{1, 2, . . . , M} denotes rotation angle 127(m) of slit 121 about an axis substantially perpendicular to at least a portion of detector 124. Integer M is, for example, between sixty and one-hundred eighty, which corresponds to three degrees per angular step and one degree per angular step, respectively. Detector 124 may corotate with slit collimator 122.

Rotation angle 127 may be a relative angle between slit collimator 122 and an object being imaged. Accordingly, rotation angle 127 may be changed by rotating the object being imaged with respect to slit collimator 122, or vice versa. Herein, reference to a changing rotation angle 127 corresponds to rotation of at least one of (a) slit collimator 122 and (b) the object being imaged, where rotations occur about an axis substantially perpendicular to at least a portion of detector 124.

Data processor 130 includes a memory 132, microprocessor 134, and software 140. Memory 132 may be transitory and/or non-transitory and may represent one or both of volatile memory (e.g., SRAM, DRAM, other volatile memory, or any combination thereof) and non-volatile memory (e.g., FLASH, ROM, magnetic media, optical media, other non-volatile memory, or any combination thereof). Software 140 includes machine-readable instructions. Microprocessor 134 is adapted to execute the instructions to perform functions of rotating-slit gamma-ray imager 100 as described herein. Microprocessor 134 may be a digital signal processor such as an image processor.

Software 140 includes a sinogram generator 141, an image reconstructor 142, and optionally a volume-image reconstructor 143. Sinogram generator 141 generates a sinogram 151(1) from one-dimensional images 129(1-M) and optionally generates sinograms 151(2-N) from respective one-dimensional images 129(1-M, 2-N). Image reconstructor 142 generates a reconstructed image 152(1) from sinogram 151(1) and optionally generates respective reconstructed images 152(2-N) from sinograms 151(2-N).

Image reconstructor 142 may implement an iterative algorithm. The iterative algorithm may include at least one of an expectation-maximization algorithm, a maximum likelihood estimation method, maximum a posteriori reconstruction, an algebraic reconstruction technique, a Landweber reconstruction algorithm, and a stochastic optimization method. Examples of stochastic optimization method include simulated annealing, evolutionary algorithms, and swarm algorithms.

In an embodiment, a sinogram of reconstructed image 152(1), generated at least in part by computing a Radon transform of image 152, differs from sinogram 151(1) by less than a predetermined tolerance. The predetermined tolerance, for example, functions as a convergence criterion for the iterative algorithm. In an embodiment, image reconstructor 142 implements an iterative algorithm that minimizes a merit function, such as an $L^1$-norm or an $L^2$-norm, or maximizes a merit function such as likelihood function.

Optional volume-image reconstructor 143 generates a reconstructed volume-image 153 from reconstructed images 152. Volume-image reconstructor 143 implements a tomographic construction algorithm, for example. The tomographic construction algorithm may include at least one of a filtered back projection algorithm, MLEM, an algebraic reconstruction technique, a Landweber reconstruction algorithm, and a maximum a posteriori reconstruction technique.

Data processor 130 may also include a hardware controller 136 that controls the angular orientation of slit collimator 122. In an embodiment, rotating-slit gamma-ray imager 100 does not include data processor 130, but is communicatively coupled with data processor 130 remotely located from rotating-slit gamma-ray imager 100. In such an embodiment, rotating-slit gamma-ray imager 100 and data processor 130 may be communicatively coupled via wireless or wired communication protocols known in the art. In such an instance, data processor 130 may operate as a post-processing unit compatible for processing images generated by one or more types of rotating-slit gamma-ray imagers.

Figure 2:
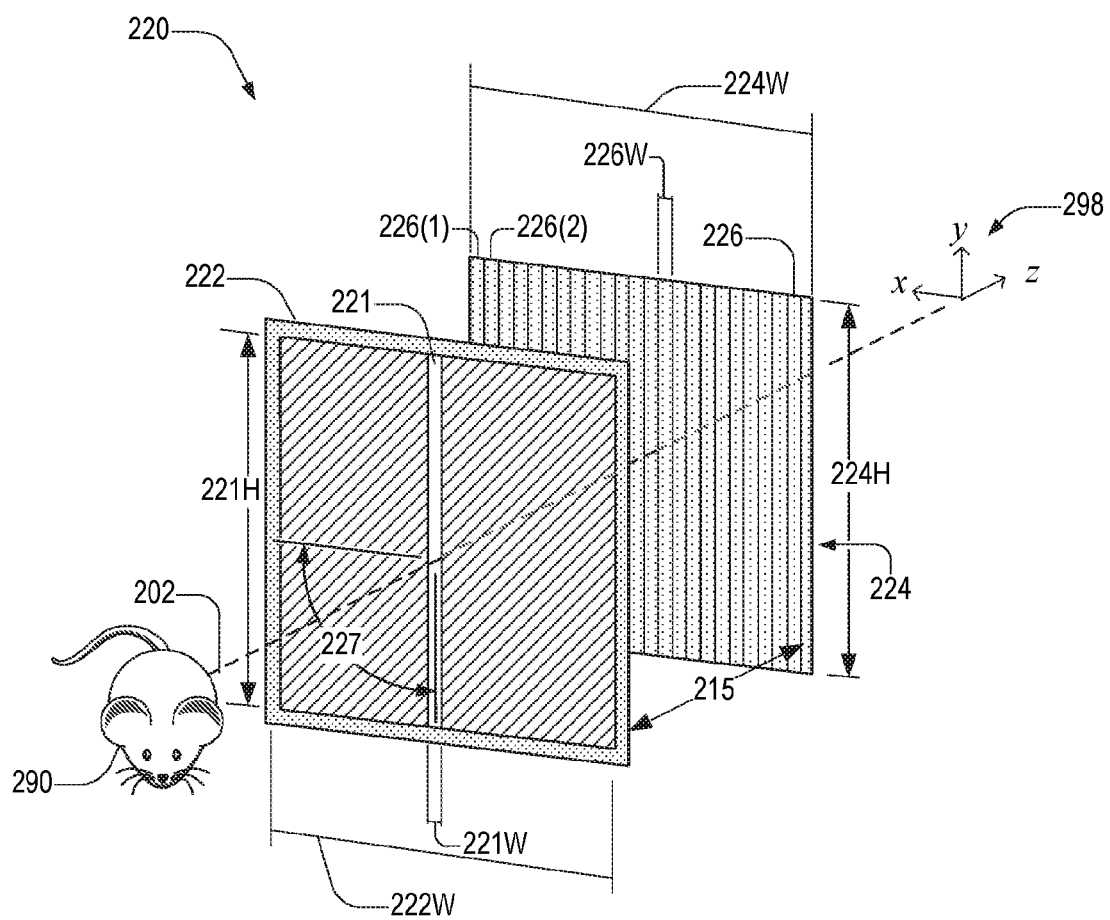
FIG. 2 illustrates an example of the imaging assembly of the rotating-slit gamma-ray imager of FIG. 1.

FIG. 2 illustrates an imaging assembly 220 imaging a subject 290. Imaging assembly 220 is an example of imaging assembly 120 of FIG. 1. Imaging assembly 220 includes a rotating-slit collimator 222 and a detector 224, which are examples of collimator 122 and detector 124, respectively.

Collimator 222 may be formed of a material that blocks gamma rays and includes a slit 221. Slit 221 has a slit width 221W and a slit height 221H in the x and y directions respectively in a coordinate system 298. Herein, directions x,y, and z are with reference to coordinate system 298 unless otherwise specified.

Detector 224 has a plurality of oblong pixels 226(p) in a plane parallel to the x-y plane. Integer p is a pixel index in the x direction, each pixel 226 has a width 226W. The long dimension of the pixels 226 are aligned with slit 221. For clarity of illustration, not all pixels 226 are labeled in FIG. 2. Pixels 226 may include a semiconductor material suitable for detection of gamma rays, such as cadmium zinc telluride (CdZnTe or CZT).

In an exemplary mode of operation of imager 100 that includes at least one imaging assembly 220, at least one of imaging assembly 220 and subject 290 rotate about a rotation axis 202. For example, imaging assembly 220 rotates while subject 290 remains stationary. Alternatively, imaging assembly 220 remains stationary while subject 290 rotates. In either case, imaging assembly 220 may be mechanically configured such that each pixel 226 remains parallel to slit 221 during rotation. Herein, slit 221 being parallel to pixels 226 is equivalent to slit-collimator 222 being parallel to pixels 226. Rotation axis 202 is substantially perpendicular to a plane that includes pixels 226, for example, a front surface of detector 224.

Collimator 222 has a rotation angle 227, which corresponds to the orientation of slit 221 with respect to the x direction. Rotation angle 227 is an example of rotation angle 127 (FIG. 1). In FIG. 2, slit 221 is oriented parallel to the y-direction for illustrative purposes only.

Both slit width 221W and slit height 221H of slit 221 may be adjustable. An adjustable width enables adaptive imaging, e.g., for multiple resolution requirements. An adjustable height enables control of image artifacts when forming reconstructed volume-image 153. One source of artifacts is stray light, such as electromagnetic radiation reaching detector 224 outside the field of view of imaging assembly 220.

During acquisition of one-dimensional images 129, rotation of imaging assembly 220 or subject 290 may either have continuous smooth motion or discrete motion, where rotation occurs in steps with momentary pauses therebetween. One-dimensional images 129 may be acquired with uniform sampling, for example, corresponding to uniformly-spaced rotation angles between 0° and 360°. Alternatively, angular sampling may be non-uniform, which enables adaptive angular sampling.

Rotating-slit collimator 222 and detector 224 are each in planes substantially parallel to the x-y plane and separated by a distance 215 along the z-direction. Distance 215 may also be adjustable, which also allows for adaptive imaging. Rotation axis 202 intersects the center of slit collimator 222, and is substantially perpendicular to the x-y plane. Herein, substantially parallel and substantially perpendicular may include, but is not limited to, within ±5° of being parallel and perpendicular, respectively.

Rotating-slit collimator 222 has a width 222W in the x direction. Detector 224 has a width 224W in the x direction and height 224H in the y direction. In an embodiment, widths 222W, 224W and heights 221H, 224H are each 100 mm, slit width 221W is 0.3 mm, width 226W is 0.1 mm, and distance 215 is 100 mm.

Detector 224 may be replaced with a two-dimensional array of pixels without departing from the scope hereof. Each pixel of such a two-dimensional array has an aspect ratio of less than two, for example. The two-dimensional pixel array may corotate with rotating-slit collimator 222 such that each row of pixels or column of pixels is parallel to slit 221 for any rotational orientation of slit 221. Alternatively, the 2-D detector may be stationary with respect to a rotational orientation of slit 221 such that pixels of the 2-D detector are grouped according to the angle of slit 221. For example, a line parallel to slit 221 intersects a plurality of pixels, the plurality of pixels forming the group. The contribution of each pixel of the group, to a one-dimensional image 129, depends in part on where the line intersects the pixel, e.g., the pixel's center or corner.

In an embodiment, detector 224 is also translatable in the x-y plane, for example, in a direction perpendicular to the angular orientation of slit 221. Such lateral movement enables dynamic tracking of a region of interest of subject 290, for example, during rotation of one or both of slit-collimator 222 and detector 224. The amplitude of lateral movement in the x-y plane may be in part determined by a trigonometric function of rotation angle 227. For example, the magnitude is proportional to the sine or cosine of rotation angle 227.

Figure 3:
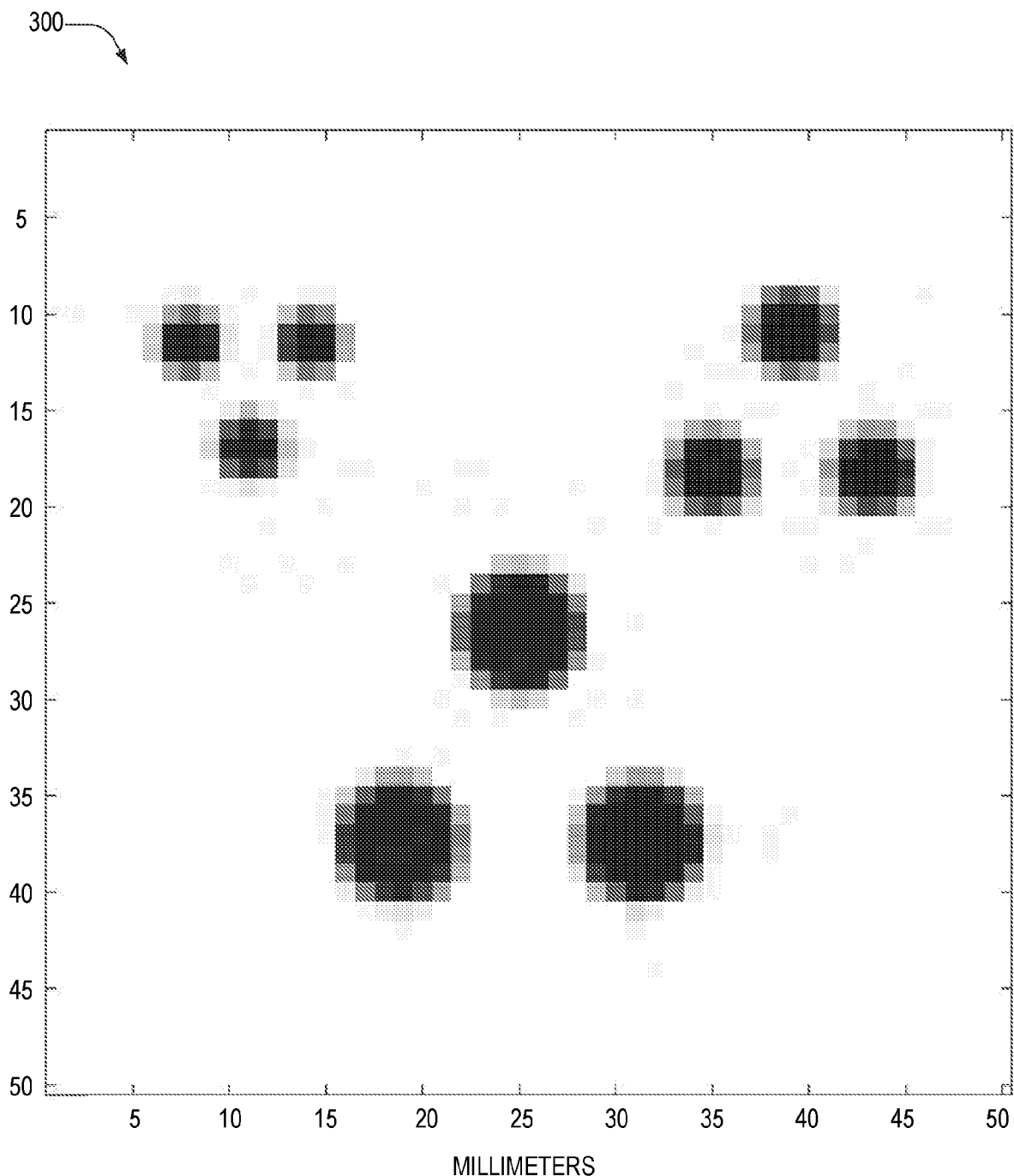
FIG. 3 is a transverse cross-sectional view of a digital phantom used to simulate operation of the rotating-slit gamma-ray imager of FIG. 1, in an embodiment.

FIG. 3 is a transverse cross-sectional view of a digital phantom 300 used to simulate operation of rotating-slit gamma-ray imager 100. Digital phantom 300 includes nine hot (radioactive) rods of three different diameters.

Figure 4:
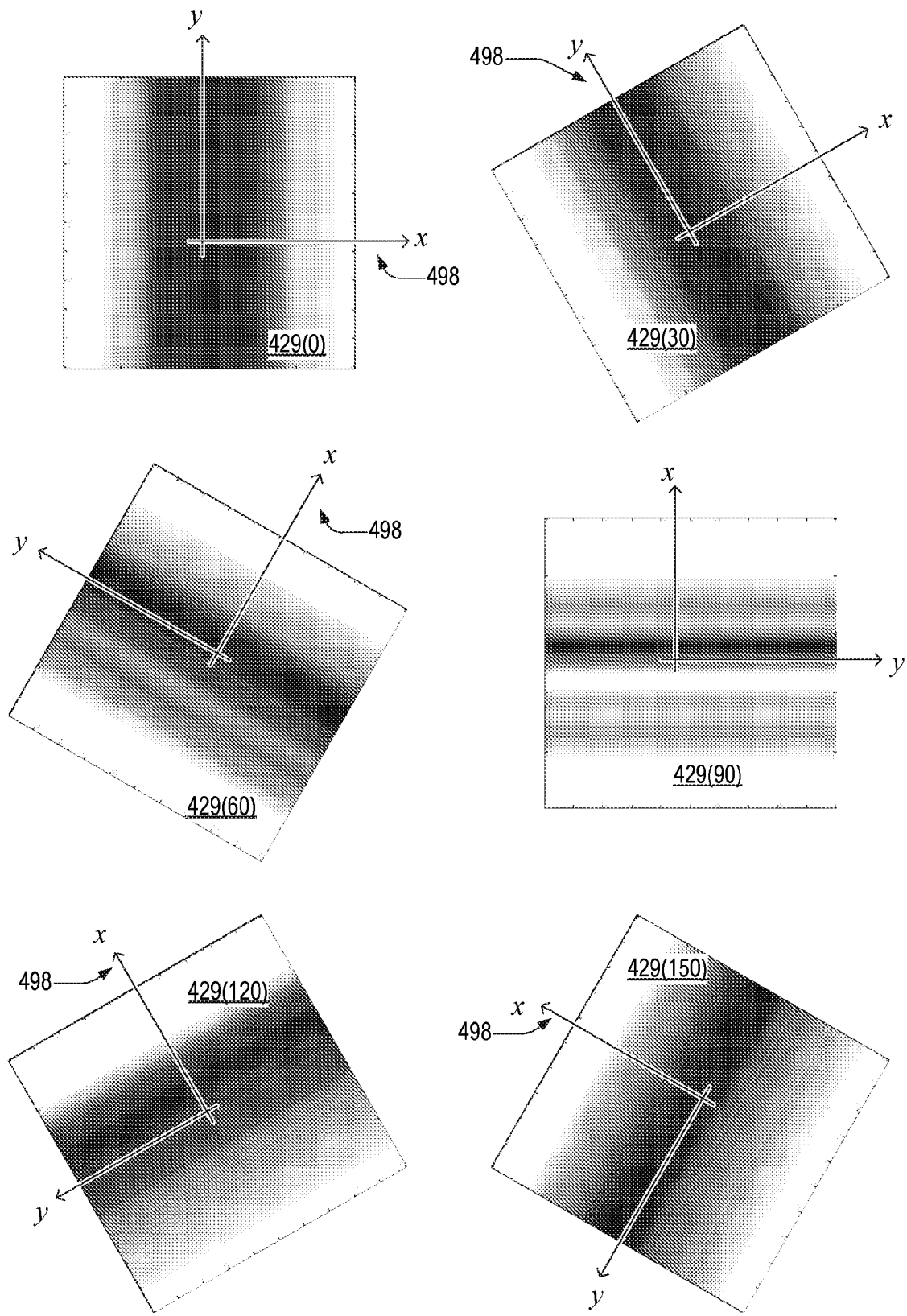
FIG. 4 illustrates a selected plurality of one-dimensional images of the digital phantom of FIG. 3 captured by the imaging assembly of FIG. 2.

FIG. 4 illustrates a selected plurality of one-dimensional images 429 of digital phantom 300 captured by imaging assembly 220. Images 429 were captured with imaging assembly 220 oriented such that rotation axis 202 intersects the axes of the rods of phantom 300 at a 45° angle. One-dimensional images 429 are each an example of one-dimensional image 129, and correspond to a different rotation angle 227. FIG. 4 illustrates one-dimensional images 429(0, 30, 60, 90, 120, 150), which correspond to respective rotation angles $\theta_m=\{0°, 30°, 60°, 90°, 120°, 150°\}$. Images 429(0, 30, 60, 90, 120, 150) are part of a full-set of ninety of images 429 captured at ninety evenly-spaced rotation angles $\theta_m \in \{0°, 2°, \ldots, 176°, 178°\}$.

In FIG. 4, a two-dimensional x-y coordinate system 498 is superimposed on each one-dimensional image 429 such that the x axis and y axis are oriented, respectively, perpendicular and parallel to the respective slit rotation angle of each image 429. As in coordinate system 298 of FIG. 2, x=0 of coordinate system 498 corresponds to the region of an image 429 aligned with slit 221. Each image 429($\theta_m$) has respective pixel values $p_{\theta_m}(x,y)$ shown in FIG. 4 as a gray-scale map.

In response to uniform illumination of slit 221, pixel values $p_{\theta_m}(x,y)$ decrease as a function of distance from slit 221 according to an illumination falloff function that varies with x. An exemplary illumination falloff function is $E(x)=\cos(\phi)$, where $\tan(\phi)=x/L$ and L is distance 215. Hence, $E(x)=L/\sqrt{x^2+L^2}$.

If imaging assembly 220 is rotated through a set of rotation angles 227 spanning a 180° range, the data from detector 224 can be arranged into a sinogram, with one axis representing the pixel index of 1-D detector 124, and the other axis representing the rotation angle. In embodiments of rotating-slit gamma-ray imager 100 that include a stationary 2-D detector instead of detector 124, forming a sinogram can be accomplished with suitable combinations of pixels.

Figure 5:
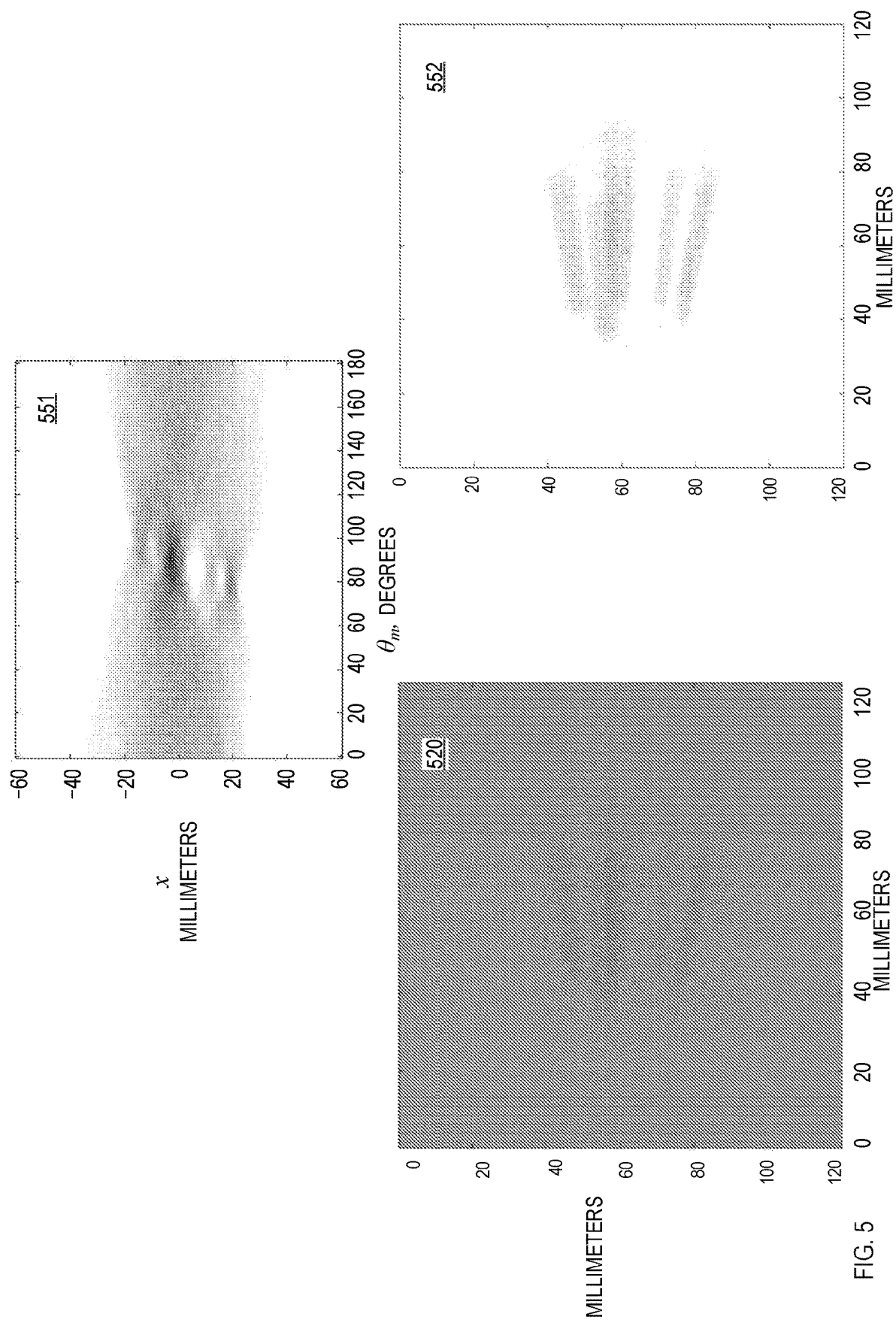
FIG. 5 shows an exemplary sinogram (left), its inverse-Radon-transform image (middle), and a Maximum-Likelihood Expectation Maximization (MLEM) reconstructed image (right).

FIG. 5 shows an exemplary sinogram 551 and its corresponding inverse-Radon-transform image 520, and a reconstructed image 552. Sinogram 551 is an example of sinogram 151 and is a sinogram of the ninety of images 429. Inverse-Radon-transform image 520 is generated via filtered back projection. Reconstructed image 552 is an example of reconstructed image 152. Image 552 was generated via sixty iterations of a MLEM reconstruction method. Images 520 and 552 were both generated in-part from the ninety one-dimensional images 429 discussed above regarding FIG. 4.

Image 552 has a trial sinogram that differs from sinogram 551 by less than a predetermined tolerance of the MLEM reconstruction method. The trial sinogram is, in part, the result of processing image 552 with a Radon transform and operations that remove effects of the aforementioned illumination falloff function E(x).

Sinogram 551 has a plurality of intensity values $S_{551}(\theta_m, x)$, where $\theta_m$ and x are defined in FIG. 4. For a given rotation angle $\theta_m$ sinogram 551 has intensity values $S_{551}(\theta_m,x)=\int p_{\theta_m}(x,y)dy$. Without departing from the scope hereof, intensity values $S_{551}(\theta_m,x)$ may be proportional to $\int p_{\theta_m}(x,y)dy$ or a discrete sum $\Sigma_y p_{\theta_m}(x,y)$.

When the Poisson noise is high due to a shortened data acquisition duration at each angle, the inverse Radon transform (e.g., via filtered back projection) performs poorly. A comparison of images 520 and 552 illustrates this, as image 520, resulting from an inverse Radon transform, has less contrast and more noise than image 552. However, if an iterative reconstruction method (such as MLEM) that enforces positivity is applied, the reconstructed image is improved relative to both image 520 but also a physical pinhole image acquired in the same total acquisition time, as FIG. 6 illustrates.

Figure 6:
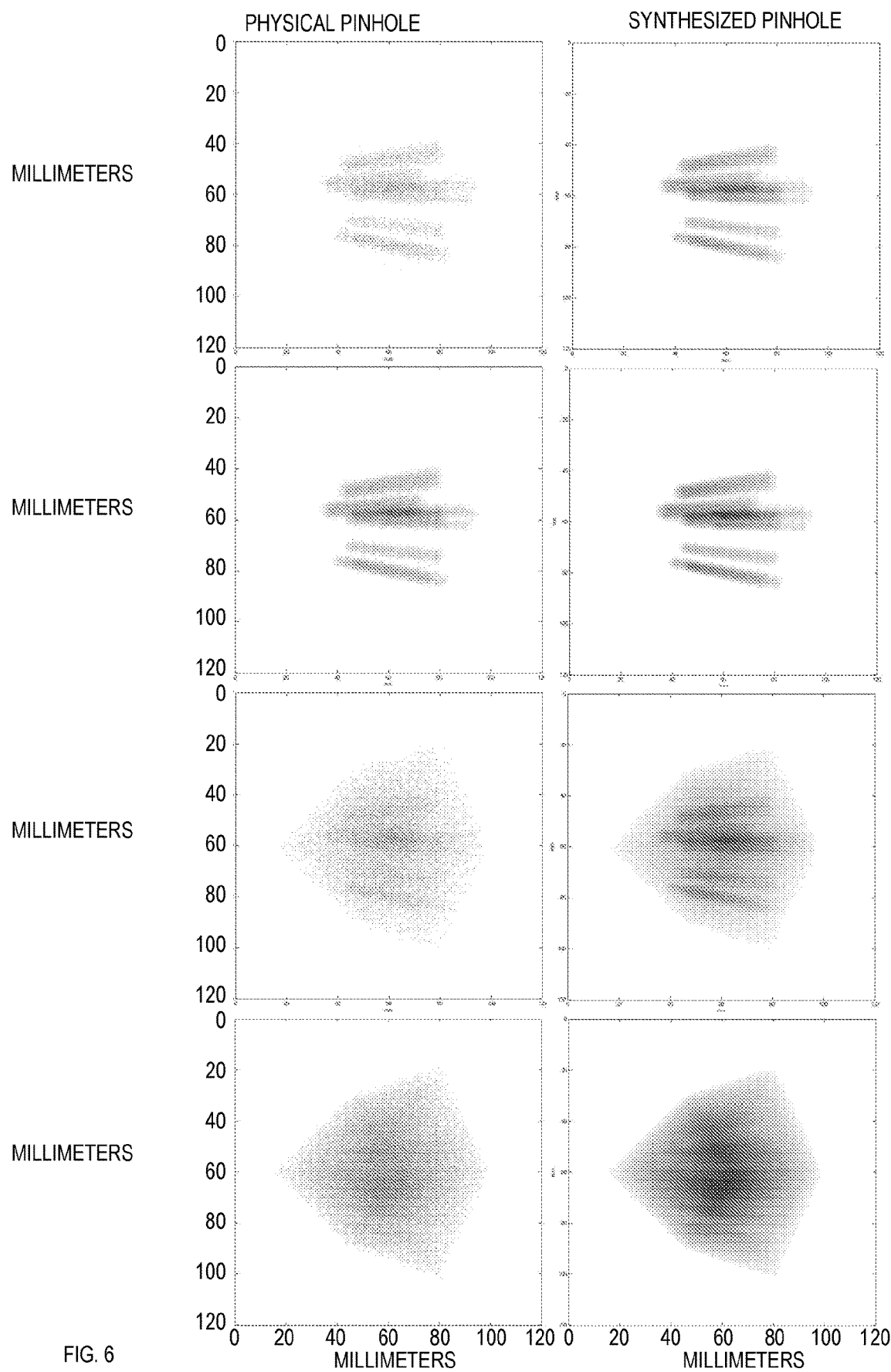
FIG. 6 is a comparison between physical pinhole aperture images and exemplary synthesized virtual pinhole images, the latter formed by an embodiment of the rotating-slit gamma-ray imager of FIG. 1.

FIG. 6 is a comparison between physical pinhole aperture images (left column) and synthesized virtual pinhole images (right column). For each row, the data acquisition time is the same. The second row's acquisition time is ten times that of the first row. The phantom in the third row is immersed in a cube-shape background (20% of the peak radioactivity of the hot rods). The phantom in the fourth row contains cold rods immersed in the background activity. The synthesized virtual pinhole images of FIG. 6 are examples of a two-dimensional reconstructed image 152.

Figure 7:
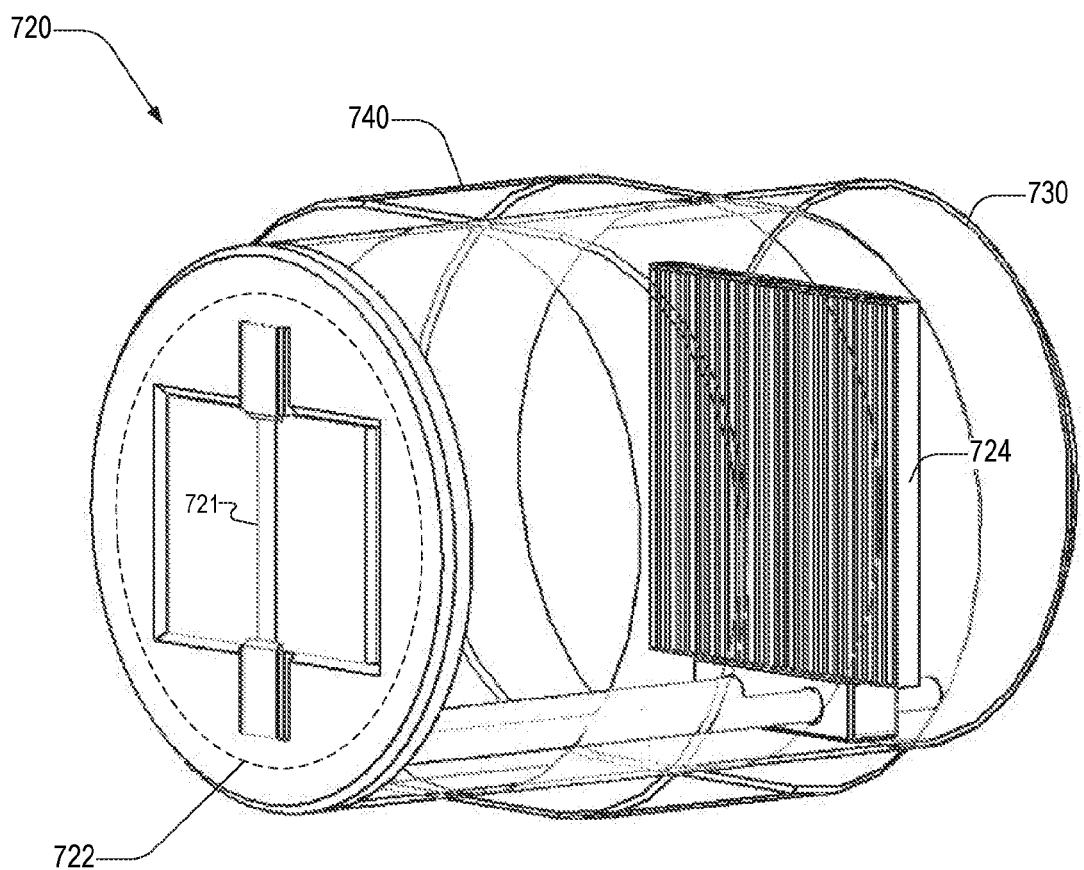
FIG. 7 is a perspective view of a second example of the imaging assembly of the rotating-slit gamma-ray imager of FIG. 1.

FIG. 7 is a perspective view of an imaging assembly 720, which is an example of imaging assembly 120 shown in FIG. 1. Imaging assembly 720 includes a slit collimator 722 and a detector 724, which are examples of slit collimator 122 and detector 124, respectively. Slit collimator 722 includes a slit 721, which is an example of slit 121. Imaging assembly 720 also includes a housing 730 and a base 740. Slit collimator 722 and detector 724 are mechanically attached to housing 730, which is configured to rotate in base 740 such that slit collimator 722 and detector 724 corotate.

Figure 8:
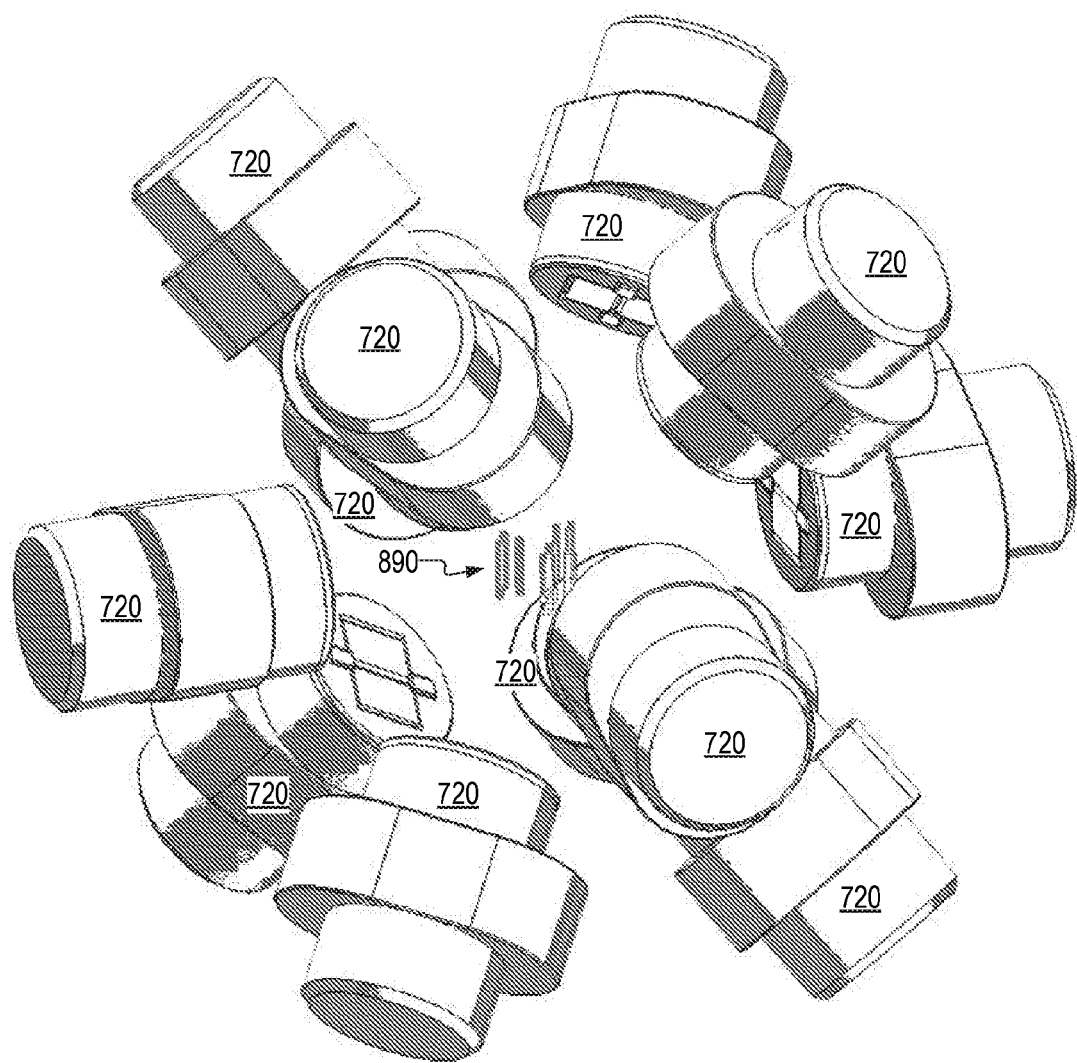
FIG. 8 is a perspective view of twelve imaging assemblies of FIG. 7 arranged to have a common overlapping field of view, in an embodiment.

FIG. 8 is a perspective view of twelve imaging assemblies 720, which are collectively an example of imaging assemblies 120(1-N) of rotating-slit gamma-ray imager 100, where N=12. Imaging assemblies 720 have respective viewing angles of a subject 890. The viewing angles are examples of viewing angles 128.

Figure 9:
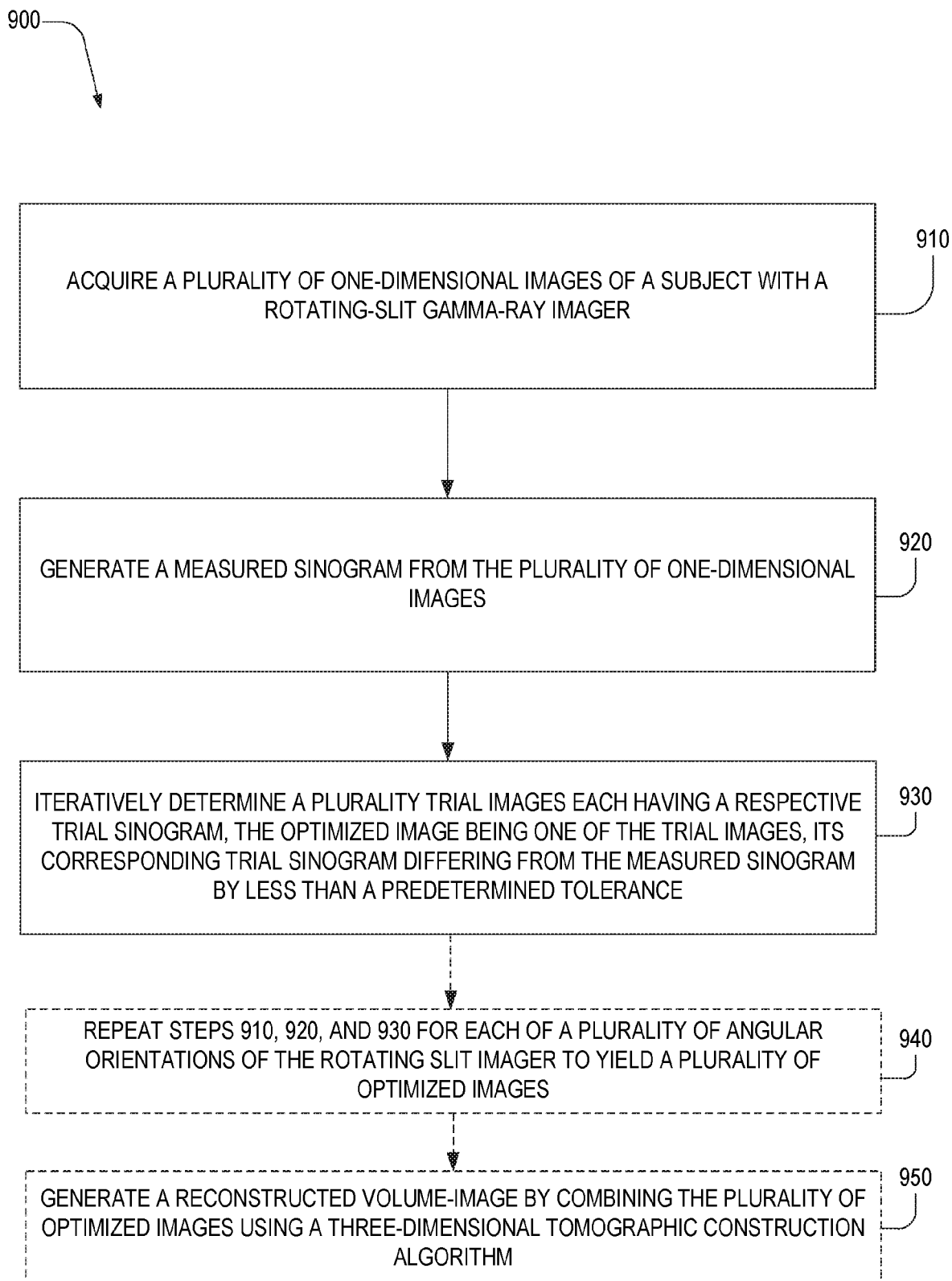
FIG. 9 is a flowchart illustrating a method for forming an optimized image, in an embodiment.

FIG. 9 is a flowchart illustrating a method 900 for forming an optimized image of a subject. Method 900 may be implemented within one or more aspects of rotating-slit gamma-ray imager 100. For example, method 900 is implemented by microprocessor 134 executing computer-readable instructions of software 140, shown in FIG. 1.

In step 910, method 900 acquires a plurality of one-dimensional images of a subject with a rotating-slit gamma-ray imager having a detector and a slit collimator. Each one-dimensional image corresponds to a different relative angular orientation of the slit collimator and the subject about a longitudinal axis substantially perpendicular to a front surface of the detector. In an example of step 910, rotating-slit gamma-ray imager 100 acquires one-dimensional images 429.

In step 920, method 900 generates a measured sinogram from the plurality of one-dimensional images. In an example of step 920, sinogram generator 141 of rotating-slit gamma-ray imager 100 generates sinogram 551 of FIG. 5.

In step 930, method 900 iteratively determines a plurality of trial images each having a respective trial sinogram. The optimized image is one of the trial images and has a corresponding trial sinogram differing from the measured sinogram by less than a predetermined tolerance. In an example of step 930, image reconstructor 142 of data processor 130 generates a two-dimensional reconstructed image 552.

Step 940 is optional. In step 940, method 900 repeats steps 910, 920, and 930 for each of a plurality of additional angular orientations of the subject relative to either the rotating-slit imager or an additional rotating-slit imager. Step 940 results in a plurality of optimized images. In an example of step 940, each imaging assembly 720 in the figuration of FIG. 8 generates a respective optimized image of subject 890.

Step 950 is optional. In step 950, method 900 generates a reconstructed volume-image by combining the plurality of optimized images using a three-dimensional tomographic construction algorithm. In an example of step 950, volume-image reconstructor 143 of data processor 130 generates reconstructed volume-image 153.

FIG. 10 shows an experimental setup 1095 for a demonstration of a rotating-slit gamma-ray imager 1000, which is an embodiment of rotating-slit gamma-ray imager 100. Rotating-slit gamma-ray imager 1000 includes an intensified quantum-imaging detector (iQID) camera 1020 that is downward-facing above an adjustable-slit collimator 1022 having a slit 1021. Slit 1021 is an example of slit 121. iQID camera 1020 includes a detector 1024 (not shown) with dimensions 30×40 mm and a resolution of approximately 0.14 mm. Camera 1020 is similar to the iQID camera discussed in "The iQID camera: An ionizing-radiation quantum imaging detector," Nucl. Inst. Meth. A, 767, 146-152, 2014 by Miller et al., which is incorporated herein by reference. Other cameras may be used as camera 1020 without departing from the scope hereof. Adjustable-slit collimator 1022 and detector 1024 are embodiments of adjustable-slit collimator 122 and detector 124, respectively.

In experimental setup 1095, iQID camera 1020 is 88 mm above adjustable-slit collimator 1022 and a rotation stage 1092 is located 68-mm beneath slit collimator 1022. This imaging configuration results in a magnification of 1.3. Rotation stage 1092 has a rotation axis, not labeled, that is example of rotation axis 202 of FIG. 2.

For simplicity, rotation stage 1092 rather than the slit collimator 1022 rotates to generate images. Slit 1021 of adjustable slit collimator 1022 may be set to have a 0.5-mm slit width. Slit 1021 has a length that is one hundred times its width. A corresponding physical pinhole 1014 (with dimensions 0.5×0.5 mm), may be created by adding a second orthogonal slit with the same width.

FIG. 11 is a photograph of a phantom 1100 in a holder 1120. Phantom 1100 includes six iodine-125 ($^{125}$I) seeds 1110(1-6) each having a maximum gamma-ray photon energy of approximately 36 keV.

Figure 12:
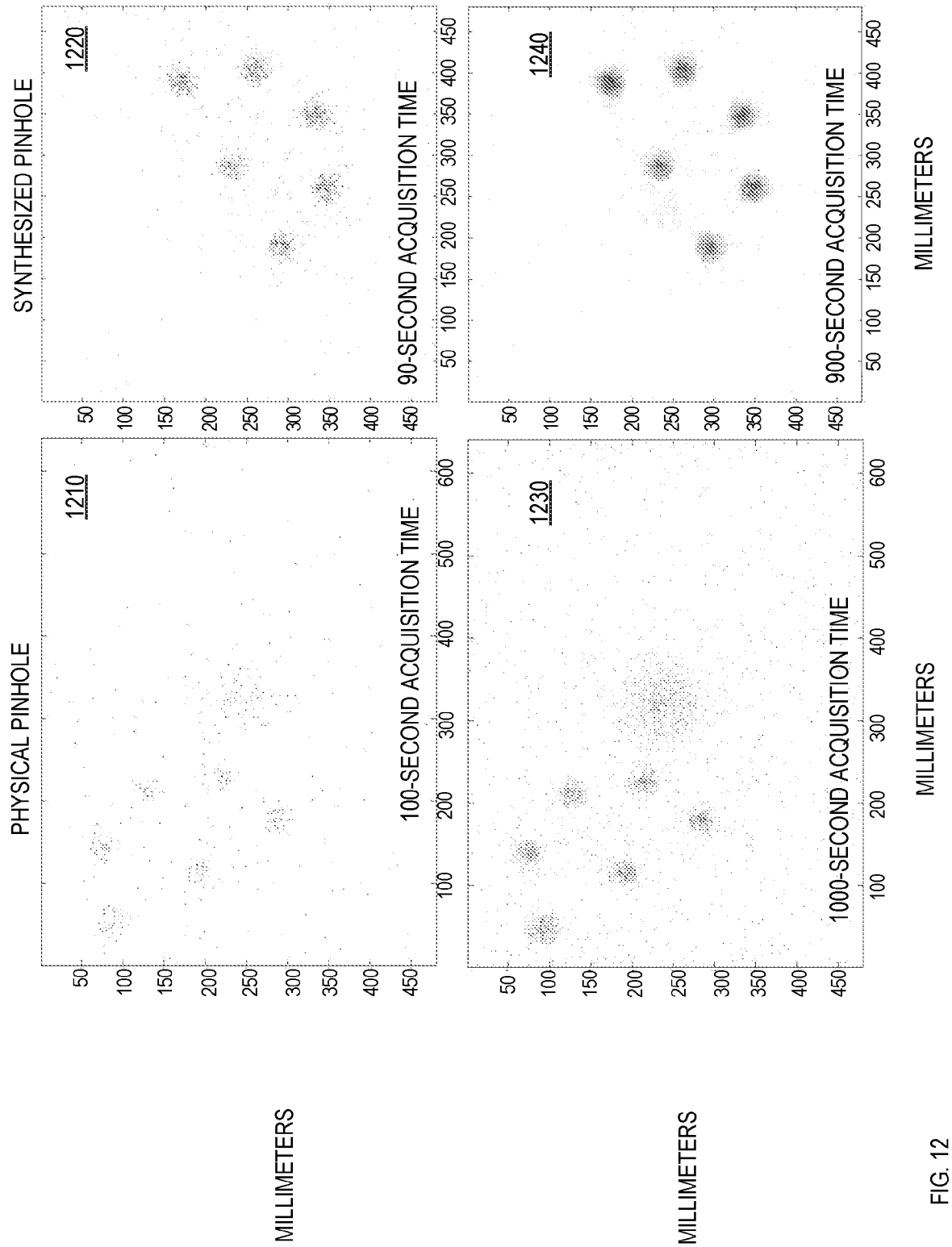
FIG. 12 shows exemplary projection images from physical-pinhole and pinhole-synthesis collimation, the latter formed by an embodiment of the rotating-slit gamma-ray imager of FIG. 1.

FIG. 12 shows projection images 1210, 1220, 1230, and 1240 from physical-pinhole and pinhole-synthesis collimation corresponding to experimental setup 1095 with phantom 1100 on rotation stage 1092. Projection images 1220 and 1240 are synthesized virtual pinhole projection images corresponding to physical pinhole projection images 1210 and 1230 respectively. Projection images 1210, 1220, 1230, and 1240 result from acquisition times of 100 seconds, 90 seconds, 1000 seconds, and 900 seconds, respectively.

Projection images 1210 and 1230 are projection images from physical pinhole 1014 having dimensions 0.5×0.5 mm. Projection images 1220 and 1240 are reconstructed projection images from a synthesized virtual pinhole, that is, a pinhole synthesized from slit-aperture imager 1000, with slit width 1021W equal to 0.5 mm, having captured multiple one-dimensional images 129 of phantom 1100 at different slit rotation angles.

Projection images 1220 and 1240 are reconstructed by data processor 130, using an iterative MLEM method that enforces positivity, from a plurality of one-dimensional images 129 corresponding to different angular orientations of phantom 1100, via rotation of rotation stage 1092. Projection images 1220 and 1240 are each examples of a two-dimensional reconstructed image 152.

Projection images 1220 and 1240 have the same resolution as images 1210 and 1230 respectively. That is, the center of rotation of slit 1021, in the generation of projection images 1220 and 1240, corresponds to the location of physical pinhole 1014 used to generate projection images 1210 and 1230, respectively. The total sensitivity of projection images 1220 and 1240 is enhanced—the additional sensitivity being afforded by slit 1021 having a slit width 1021W (0.5-mm in this example) approximately equal to the effective diameter of pinhole 1014—but with a much longer length. Although pinhole 1014 is square, its equivalent diameter is close to 0.5 mm.

Figure 13:
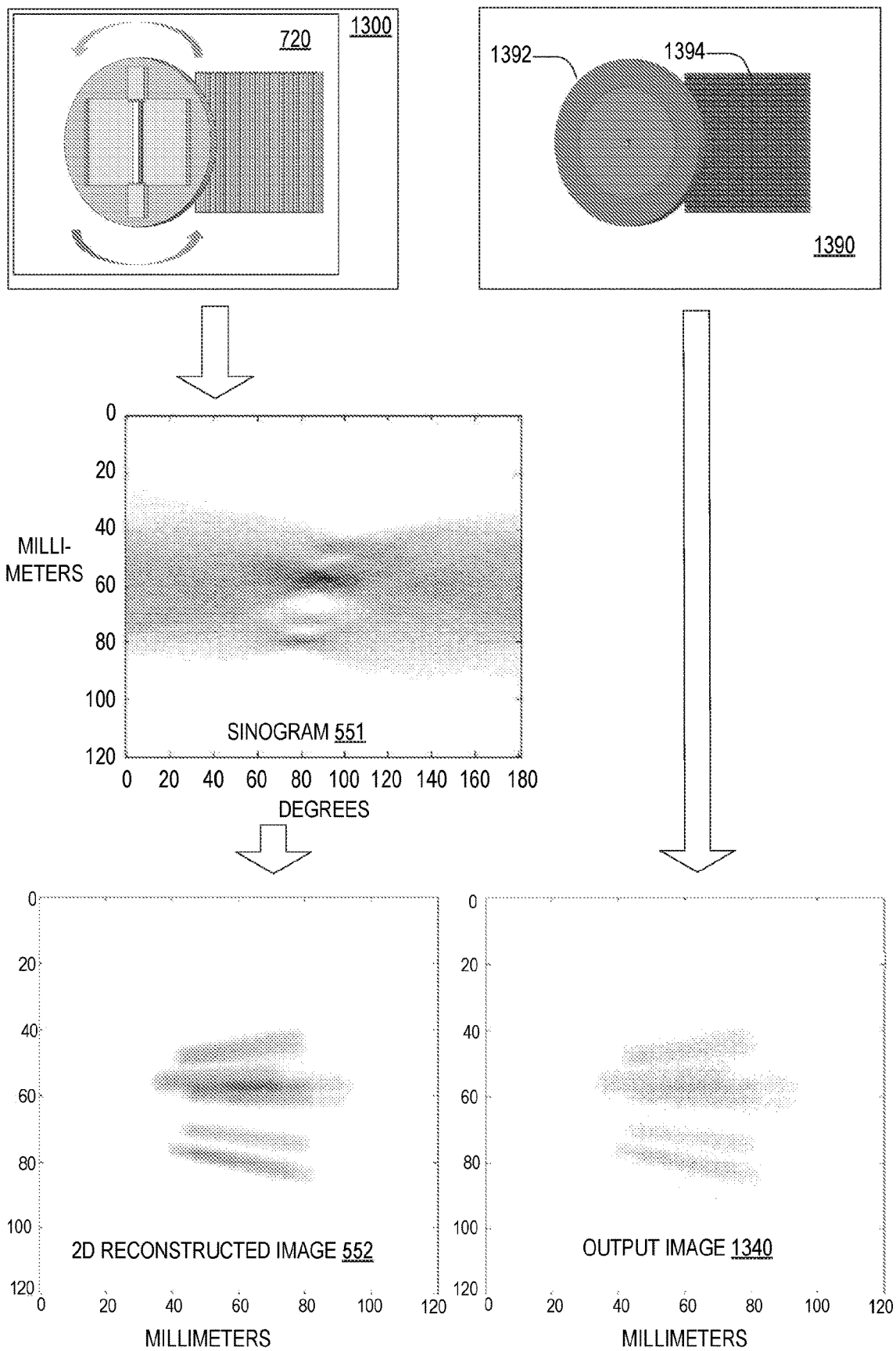
FIG. 13 illustrates a comparison of image acquisition via an embodiment of the rotating-slit gamma-ray imager of FIG. 1 and a pinhole gamma-ray imager.

FIG. 13 illustrates a comparison of image acquisition via a rotating-slit gamma-ray imager 1300 and a traditional pinhole gamma-ray imager 1390. Rotating-slit gamma-ray imager 1300 includes imaging assembly 720 of FIG. 7.

Traditional pinhole gamma-ray imager 1390 includes a pinhole aperture 1392 and a two-dimensional pixel array 1394. Output image 1340 is acquired directly from traditional pinhole gamma-ray imager 1390. By contrast, rotating-slit gamma-ray imager 100 generates sinogram 551, discussed above with respect to FIG. 5. Image 552 is reconstructed from sinogram 551 using sixty iterations of a MLEM reconstruction algorithm.

Figure 14:
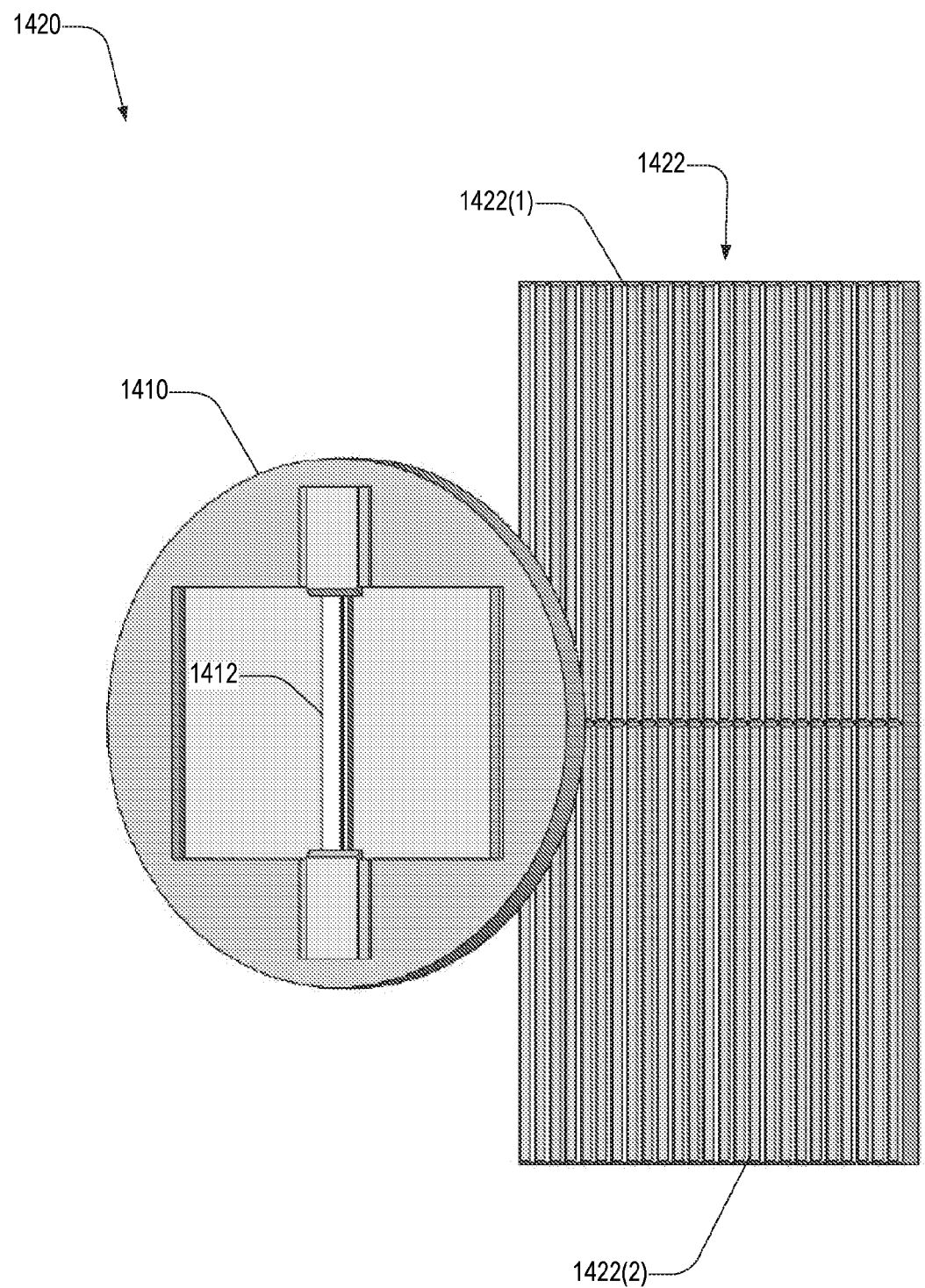
FIG. 14 is a perspective view of a third example of the imaging assembly of the rotating-slit gamma-ray imager of FIG. 1.

FIG. 14 illustrates an imaging assembly 1420 that includes a slit collimator 1410 and an elongated detector 1422. Slit collimator 1410 includes a slit 1412. Elongated detector 1422 is for example two adjacent detectors 1422 (1,2). Imaging assembly 1420 is an example of imaging assembly 120 of FIG. 1. The relatively increased length of elongated detector 1422 enables an embodiment of rotating-slit gamma-ray imager 100 that includes imaging assembly 1420 to detect more gamma-ray producing events than with a conventional smaller detector, which result in enhanced detection sensitivity.

FIG. 15 illustrates an imaging assembly 1520 that includes slit collimator 1410 and an extra-wide detector 1522. Extra-wide detector 1522 is for example two detectors side-by-side. Imaging assembly 1520 is an example of imaging assembly 120 of FIG. 1. The relatively increased width of extra-wide detector 1522 enables an embodiment of rotating-slit gamma-ray imager 100 that includes imaging assembly 1520 to obtain larger images by increasing axial distance between slit collimator 1410 and detector 1522. The increased width of detector 1522 enables creation of large images with enhanced field-of-view without sacrificing spatial resolution.

Combinations of Features:

Features described above as well as those claimed below may be combined in various ways without departing from the scope hereof. The following examples illustrate some possible, non-limiting combinations:

(A1) A method for forming an optimized image of a subject includes steps of acquiring a plurality of one-dimensional images, generating a measured sinogram from the plurality of one-dimensional images, and determining a plurality of trial images. In the step of acquiring, the method acquires a plurality of one-dimensional images of the subject captured by a rotating-slit imager having (a) a detector, and (b) a slit collimator having a slit oriented at one of a respective plurality of slit-rotation angles, relative to the subject, about a longitudinal axis substantially perpendicular to a front surface of the detector. In the step of determining, the method iteratively determines a plurality of trial images each having a respective trial sinogram. The optimized image is one of the plurality of trial images and its corresponding trial sinogram differs from the measured sinogram by less than a predetermined tolerance.

(A2) In the method denoted by (A1), each of the plurality of slit-rotation angles being denoted by a respective angle $\theta_m$, and the one-dimensional image corresponding to $\theta_m$ having pixel values $p_{\theta_m}(x,y)$, the measured sinogram may have pixel values $S_1(\theta_m,x)=\int p_{\theta_m}(x,y)dy$, where x and y are locations along transverse axes that are (a) perpendicular to and parallel to the slit, respectively, and (b) substantially orthogonal to the longitudinal axis.

(A3) In any method denoted by one of (A1) and (A2), the step of iteratively determining may include generating each respective trial sinogram at least in part by computing a Radon transform on the respective trial image.

(A4) In any method denoted by one of (A1) through (A3), the iteratively determining may be performed, in part, by imposing a positivity constraint such that each of the plurality of trial images has a respective plurality of pixel values representing a positive photon count.

(A5) In any method denoted by one of (A1) through (A4), the step of iteratively determining may be performed, in part, according to at least one of an expectation-maximization algorithm and a maximum likelihood estimation method.

(A6) In any method denoted by one of (A1) through (A5), the step of iteratively determining may be performed, in part, according to at least one of a maximum a posteriori reconstruction, an algebraic reconstruction technique, a Landweber reconstruction algorithm, and a stochastic optimization method.

(A7) Any method denoted by one of (A1) through (A6), in which the subject is at a first angular orientation relative to the rotating-slit imager, may further include, for each of a plurality of additional angular orientations of the subject relative to either the rotating-slit imager or an additional rotating-slit imager, steps of (i) repeating the step of acquiring, (ii) repeating the step of generating, and (iii) repeating the step of iteratively determining to yield a plurality of additional optimized images corresponding to the plurality of additional angular orientations.

(A8) The above method denoted by (A7) may further include generating a reconstructed volume-image by combining the plurality of optimized images using a three-dimensional tomographic construction algorithm.

(B1) A rotating-slit gamma-ray imager includes (i) a detector having an array of pixels, (ii) a slit collimator, (iii) a memory storing non-transitory computer-readable instructions, and (iv) a microprocessor. The slit collimator has a slit at least partially aligned with the detector and configured to be oriented at any of a plurality of slit-rotation angles in a plane substantially parallel to the array of pixels. The microprocessor is adapted to execute the instructions to form an optimized image of a subject by implementing any of the methods denoted above as (A1) through (A8).

(B2) In the rotating-slit gamma-ray imager denoted by (B1), in which the array of pixels includes a plurality of pixel columns, the slit collimator may include a slit orientated parallel to the plurality of columns, and the slit collimator and the detector may be configured to rotate together such that the slit remains parallel to the plurality of pixel columns.

(B3) In any rotating-slit gamma-ray imager denoted by one of (B1) and (B2), each of the plurality of slit-rotation angles being denoted by a respective angle $\theta_m$, and the one-dimensional image corresponding to $\theta_m$ having pixel values $p_{\theta_m}(x,y)$, the measured sinogram may have pixel values $S_1(\theta_m,x)=\int p_{\theta_m}(x,y)dy$, where x and y are locations along transverse axes that are (a) perpendicular to and parallel to the slit, respectively, and (b) substantially orthogonal to the longitudinal axis.

(B4) Any rotating-slit gamma-ray imager denoted by one of (B1) through (B3) may further include a second detector and a second slit collimator. The second detector has a second array of pixels and having a second field of view that at least partially overlaps a first field of view of the first detector. The second slit collimator having a second slit at least partially aligned with the second detector and in a plane substantially parallel to the second array of pixels. The microprocessor may be further adapted to execute the instructions to form a second optimized image of the subject by: (i) for each of a plurality of second slit-rotation angles of the second slit, acquiring a respective one of a plurality of second one-dimensional images of the subject captured by a the second detector, (ii) generating a second measured sinogram from the plurality of second one-dimensional images, and (iii) iteratively determining a plurality of second trial images each having a respective second trial sinogram, the second optimized image being one of the second trial images, with its corresponding second trial sinogram differing from the second measured sinogram by less than a second predetermined tolerance. The microprocessor may be further adapted to execute the instructions to generate a reconstructed volume-image by combining the first and second optimized images using a three-dimensional tomographic construction algorithm.

(C1) A data processor includes (a) a memory storing non-transitory computer-readable instructions and (b) a microprocessor. The microprocessor is configured to execute the instructions to: (i) generate a measured sinogram from a plurality of one-dimensional images captured through a slit oriented at one of a respective plurality of slit-rotation angles, relative to a subject, about a longitudinal axis substantially perpendicular to a front surface of a detector, and (ii) generate an optimized image of the subject by iteratively determining a plurality of trial images each having a respective trial sinogram, the optimized image being one of the trial images, its corresponding trial sinogram differing from the measured sinogram by less than a predetermined tolerance.

(C2) In the data processor denoted by (C1), in which each of the plurality of slit-rotation angles being denoted by a respective angle $\theta_m$, and the one-dimensional image corresponding to $\theta_m$ having pixel values $p_{\theta_m}(x,y)$, the measured sinogram may have pixel values $S_1(\theta_m,x)=\int p_{\theta_m}(x,y)dy$, where x and y are locations along transverse axes that are (a) perpendicular and parallel to the slit, respectively, and (b) substantially orthogonal to the longitudinal axis.

(C3) In any data processor denoted by one of (C1) and (C2), the microprocessor may be further configured to execute the instructions to:
(i) generate a second measured sinogram from a plurality of second one-dimensional images, captured through a second detector and a second slit collimator having a slit oriented at one of a respective plurality of slit-rotation angles, relative to a subject, about a longitudinal axis substantially perpendicular to a front surface of a detector,
(ii) generate a second optimized image of the subject by iteratively determining a plurality of second trial images each having a respective second trial sinogram, the optimized image being one of the second trial images, its corresponding second trial sinogram differing from the second measured sinogram by less than a predetermined tolerance, and
(iii) generate a reconstructed volume-image by combining the first and second optimized images using a three-dimensional tomographic construction algorithm.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall there between.

What is claimed is:

1. A method for forming an optimized image of a subject comprising:
   acquiring a plurality of one-dimensional images of the subject captured by a rotating-slit imager having (a) a detector, and (b) a slit collimator having a slit oriented at one of a respective plurality of slit-rotation angles, relative to the subject, about a longitudinal axis substantially perpendicular to a front surface of the detector;
   generating a measured sinogram from the plurality of one-dimensional images; and
   iteratively determining a plurality of trial images each having a respective trial sinogram, the optimized image being one of the plurality of trial images, its corresponding trial sinogram differing from the measured sinogram by less than a predetermined tolerance.

2. The method of claim 1, each of the plurality of slit-rotation angles being denoted by a respective angle $\theta_m$, the one-dimensional image corresponding to $\theta_m$ having pixel values $p_{\theta_m}(x,y)$, the measured sinogram having pixel values $S_1(\theta_m,x)=\int p_{\theta_m}(x,y)dy$, where x and y are locations along transverse axes that are (a) perpendicular to and parallel to the slit, respectively, and (b) substantially orthogonal to the longitudinal axis.

3. The method of claim 1, the iteratively determining including generating each respective trial sinogram at least in part by computing a Radon transform on the respective trial image.

4. The method of claim 1, the iteratively determining being performed, in part, by imposing a positivity constraint such that each of the plurality of trial images has a respective plurality of pixel values representing a positive photon count.

5. The method of claim 1, the iteratively determining being performed, in part, according to at least one of an expectation-maximization algorithm and a maximum likelihood estimation method.

6. The method of claim 1, the iteratively determining being performed, in part, according to at least one of a maximum a posteriori reconstruction, an algebraic reconstruction technique, a Landweber reconstruction algorithm, and a stochastic optimization method.

7. The method of claim 1, the subject being at a first angular orientation relative to the rotating-slit imager, and further comprising, for each of a plurality of additional angular orientations of the subject relative to either the rotating-slit imager or an additional rotating-slit imager:
   repeating the step of acquiring;
   repeating the step of generating; and
   repeating the step of iteratively determining to yield a plurality of additional optimized images corresponding to the plurality of additional angular orientations.

8. The method of claim 7, further comprising:
   generating a reconstructed volume-image by combining the plurality of optimized images using a three-dimensional tomographic construction algorithm.

9. The method claim 1, the acquiring further comprising detecting, with the detector, at least one of gamma radiation and x-ray radiation originating from the subject.

10. A rotating-slit gamma-ray imager comprising:
    a detector having an array of pixels;
    a slit collimator having a slit at least partially aligned with the detector and configured to be oriented at any of a plurality of slit-rotation angles in a plane substantially parallel to the array of pixels;
    a memory storing non-transitory computer-readable instructions;
    a microprocessor adapted to execute the instructions to form an optimized image of a subject by:
    (i) acquiring, for each of the plurality of slit-rotation angles of the slit, a respective one of a plurality of one-dimensional images of the subject captured by the detector, (ii) generating a measured sinogram from the plurality of one-dimensional images, and (iii) iteratively determining a plurality of trial images each having a respective trial sinogram, the optimized image being one of the trial images, its corresponding trial sinogram differing from the measured sinogram by less than a predetermined tolerance.

11. The rotating-slit gamma-ray imager of claim 10, the array of pixels including a plurality of pixel columns, the slit collimator including a slit orientated parallel to the plurality of columns, and the slit collimator and the detector being configured to rotate together such that the slit remains parallel to the plurality of pixel columns.

12. The rotating-slit gamma-ray imager of claim 10, each of the plurality of slit-rotation angles being denoted by a respective angle $\theta_m$, the one-dimensional image corresponding to $\theta_m$ having pixel values $p_{\theta_m}(x, y)$, the measured sinogram having pixel values $S_1(\theta_m,x) = \int p_{\theta_m}(x,y)\, dy$, where x and y are locations along transverse axes that are (a) perpendicular to and parallel to the slit, respectively, and (b) substantially orthogonal to the longitudinal axis.

13. The rotating-slit gamma-ray imager of claim 10, the microprocessor further adapted to execute the instructions to, when iteratively determining, generate each respective trial sinogram at least in part by computing a Radon transform on the respective trial image.

14. The rotating-slit gamma-ray imager of claim 10, further comprising:
- a second detector having a second array of pixels and having a second field of view that at least partially overlaps a first field of view of the first detector; and
- a second slit collimator having a second slit at least partially aligned with the second detector and in a plane substantially parallel to the second array of pixels,
- the microprocessor being further adapted to execute the instructions to form a second optimized image of the subject by:
  (i) for each of a plurality of second slit-rotation angles of the second slit, acquiring a respective one of a plurality of second one-dimensional images of the subject captured by the second detector,
  (ii) generating a second measured sinogram from the plurality of second one-dimensional images, and
  (iii) iteratively determining a plurality of second trial images each having a respective second trial sinogram, the second optimized image being one of the second trial images, its corresponding second trial sinogram differing from the second measured sinogram by less than a second predetermined tolerance,
- the microprocessor being further adapted to execute the instructions to generate a reconstructed volume-image by combining the first and second optimized images using a three-dimensional tomographic construction algorithm.

15. The rotating-slit gamma-ray imager of claim 10, the array of pixels being in a plane, each of the plurality of slit-rotation angles being about an axis substantially perpendicular to the plane.

16. A data processor comprising:
- a memory storing non-transitory computer-readable instructions; and
- a microprocessor configured to execute the instructions to:
  (i) generate a measured sinogram from a plurality of one-dimensional images captured through a slit oriented at one of a respective plurality of slit-rotation angles, relative to a subject, about a longitudinal axis substantially perpendicular to a front surface of a detector, wherein generating the measured sinogram includes removing effects of an illumination falloff function E(x), where x is a distance in a direction both perpendicular to the slit and the longitudinal axis; and
  (ii) generate an optimized image of the subject by iteratively determining a plurality of trial images each having a respective trial sinogram, the optimized image being one of the trial images, its corresponding trial sinogram differing from the measured sinogram by less than a predetermined tolerance.

17. The data processor of claim 16, each of the plurality of slit-rotation angles being denoted by a respective angle $\theta_m$, the one-dimensional image corresponding to $\theta_m$ having pixel values $p_{\theta_m}(x, y)$, the measured sinogram having pixel values $S_1(\theta_m,x) = \int p_{\theta_m}(x,y)\, dy$, where x and y are locations along transverse axes that are (a) perpendicular to and parallel to the slit, respectively, and (b) substantially orthogonal to the longitudinal axis.

18. The data processor of claim 16, the iteratively determining being performed, in part, according to at least one of an expectation-maximization algorithm and a maximum likelihood estimation method.

19. The data processor of claim 16, the microprocessor being further configured to execute the instructions to:
  (i) generate a second measured sinogram from a plurality of second one-dimensional images, captured through a second detector and a second slit collimator having a slit oriented at one of a respective plurality of slit-rotation angles, relative to a subject, about a longitudinal axis substantially perpendicular to a front surface of a detector,
  (ii) generate a second optimized image of the subject by iteratively determining a plurality of second trial images each having a respective second trial sinogram, the optimized image being one of the second trial images, its corresponding second trial sinogram differing from the second measured sinogram by less than a predetermined tolerance, and
  (iii) generate a reconstructed volume-image by combining the first and second optimized images using a three-dimensional tomographic construction algorithm.

20. The rotating-slit gamma-ray imager of claim 16, the falloff function E(x) equaling $L/\sqrt{x^2+L^2}$, where L is a distance along the longitudinal axis between the slit and the detector.

* * * * *